United States Patent

Noyori et al.

Patent Number: 5,198,562
Date of Patent: Mar. 30, 1993

[54] RUTHENIUM-PHOSPHINE COMPLEX AND INTERMEDIATE FOR PRODUCING THE SAME

[75] Inventors: Ryoji Noyori; Masato Kitamura, both of Aichi; Noboru Sayo; Hidenori Kumobayashi, both of Tokyo, all of Japan; Martin F. Giles, Middlesex, England

[73] Assignee: Takasago International Corporation, Tokyo, Japan

[21] Appl. No.: 739,022

[22] Filed: Aug. 1, 1991

[30] Foreign Application Priority Data

Aug. 1, 1990 [JP] Japan .................. 2-204166

[51] Int. Cl.$^5$ ............................ C07F 15/00
[52] U.S. Cl. ................................ 556/23; 556/21
[58] Field of Search ............ 556/136, 23, 21, 20, 556/19, 13

[56] References Cited

U.S. PATENT DOCUMENTS 4,994,590 2/1991 Takaya et al. .............. 556/23 X

Primary Examiner—Arthur C. Prescott
Attorney, Agent, or Firm—Sughrue, Mion, Zinn, Macpeak & Seas

[57] ABSTRACT

A ruthenium-phosphine complex represented by formula (I):

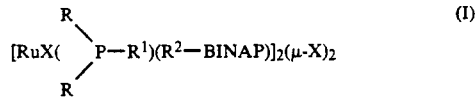

wherein $R^2$-BINAP represents a teritary phosphine compound represented by formula (II):

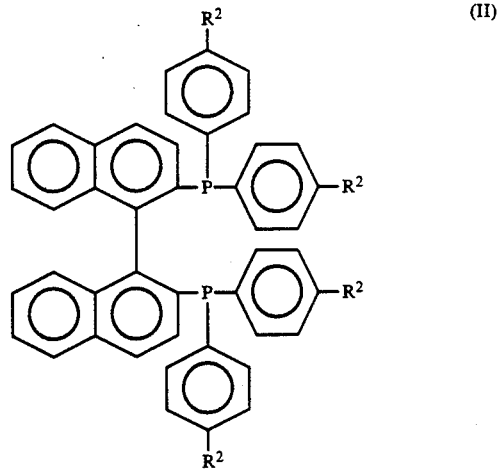

wherein $R^2$ represents a hydrogen atom, a methyl group, a methoxy group, or a t-butyl group; X represents a halogen atom; and R and $R^1$, which may be the same or different, each represent a phenyl group or a substituted phenyl group, and a ruthenium-phosphine complex represented by formula (III):

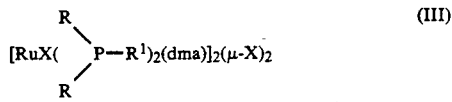

wherein R and $R^1$ are as defined above; and dma represents N,N-dimethylacetamide, which is an intermediate for synthesizing the ruthenium-phosphine complex of formula (I), are disclosed. The complex of formula (I) is useful as a catalyst for general syntheses with its ligand being an optically inactive compound or for asymmetric syntheses with its ligand being an optically active compound and, also, can be prepared at a low cost.

2 Claims, No Drawings

RUTHENIUM-PHOSPHINE COMPLEX AND INTERMEDIATE FOR PRODUCING THE SAME

FIELD OF THE INVENTION

This invention relates to a novel phosphine complex useful as a catalyst of various organic syntheses, particularly asymmetric synthesis reactions.

BACKGROUND OF THE INVENTION

A number of organic synthesis reactions using a transition metal complex as a catalyst have hitherto been developed and made use of for various purposes. In particular, many reports have been made on transition metal catalysts useful for asymmetric synthesis reactions, such as asymmetric hydrogenation and asymmetric isomerization. Among them, complexes in which an optically active tertiary phosphine compound is coordinated to a metallic rhodium are well known for asymmetric hydrogenation. For example, a rhodium-phosphine complex using 2,2'-bis(diphenylphosphino)-1,1'-binaphthyl (hereinafter abbreviated as BINAP) as a ligand is disclosed in JP-A-55-61937 (the term "JP-A" as used herein means an "unexamined published Japanese patent application"). Further, S. Inoue, et al. report that asymmetric hydrogenation of geraniol or nerol in the presence of various rhodium-phosphine complex catalysts gave citronellol having an optical purity of 66% ee.

Also, there are reports on ruthenium complexes, though fewer than on rhodium complexes. For example, known ruthenium complexes include those having BINAP or 2,2'-bis(di-p-tolylphosphino)-1,1'-binaphthyl (hereinafter abbreviated as T-BINAP) as a ligand, i.e., $Ru_2Cl_4(BINAP)_2NEt_3$ or $Ru_2Cl_4(T-BINAP)_2NEt_3$ (wherein Et represents an ethyl group, hereinafter the same) and $[RuH_l(R-BINAP)_m]X_n$ (wherein R represents a hydrogen atom or a methyl group; X represents $ClO_4$, $BF_4$, or $PF_6$; l represents 0; or 1; when l is 0, m represents 1, and n represents 2; when l is 1, m represents 2, and n represents 1) as disclosed in a publication. However, these ruthenium complexes have such disadvantageous that the preparation thereof involves complicated procedures or the yield or stability of these complexes are slightly unsatisfactory. Moreover, their catalytic activity and its duration are not deemed sufficient.

Although metallic rhodium provides excellent complex catalysts, it is expensive due to limits in place and quantity of production, so that it forms a relatively large proportion in the production cost, leading to an increased price of final products. To the contrary, metallic ruthenium is cheaper than metallic rhodium and is therefore expected to provide industrially advantageous catalysts. However, ruthenium complexes have unsolved problems with respect to reaction accuracy and applicability. Accordingly, it has been demanded to develop a catalyst which can be prepared with ease and at a low cost, which exhibits high activity for a long duration, and which achieves a high asymmetric yield, i.e., high optical purity of products, in asymmetric reactions.

SUMMARY OF THE INVENTION

In order to meet the above-described demand, the inventors have conducted extensive studies and, as a result, have found a novel highly active ruthenium complex which can be used as a catalyst for general syntheses with its ligand being an optically inactive compound or for asymmetric syntheses with its ligand being an optically active compound and, also, which can be prepared in a good yield through simple operations. The present invention has been completed based on this finding.

That is, the present invention relates to a ruthenium-phosphine complex represented by formula (I):

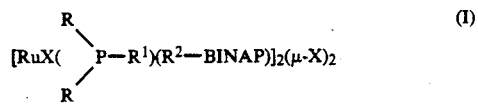

wherein $R^2$-BINAP represents a tertiary phosphine compound represented by formula (II):

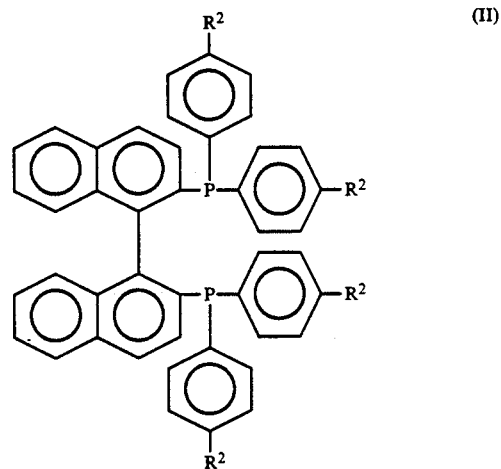

wherein $R^2$ represents a hydrogen atom, a methyl group, a methoxy group, or a t-butyl group; X represents a halogen atom; and R and $R^1$, which may be the same or different, each represent a phenyl group or a substituted phenyl group.

The present invention also relates to a ruthenium-phosphine complex represented by formula (III):

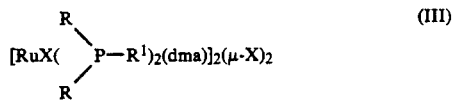

wherein R and $R^1$ are as defined above; and dma represents N,N-diemthylacetamide, which is an intermediate for synthesizing the above-described ruthenium-phosphine complex of formula (I).

DETAILED DESCRIPTION OF THE INVENTION

In formulae (I) and (III), R and $R^1$, which may be the same or different, each represent a substituted or unsubstituted phenyl group, e.g., a phenyl group; an alkyl-substituted phenyl group (e.g., 2-methylphenyl, 3-methylphenyl, 4-methylphenyl), an alkoxy-substituted phenyl group (e.g., 2-methoxyphenyl, 3-methoxyphenyl, 4-methoxyphenyl), and a dialkylaminophenyl group (e.g., 2-dimethylaminophenyl, 3-dimethylaminophenyl, 4-dimethylaminophenyl).

Of the intermediate complex compounds represented by formula (III), those wherein R and $R^1$ both represent a phenyl group (Ph) can be prepared, for example, as follows. The compound wherein X is a chlorine atom, i.e., [RuCl(PPH$_3$)$_2$-(dma)]$_2$($\mu$-Cl)$_2$ is synthesized quantitatively by allowing [RuCl$_3$(PPH$_3$)$_2$(dma)](dma) (obtainable by, for example, the process disclosed in I. S. Thorburn, S. J. Rettig, and B. R. James, *Inorg. Chem.*, Vol. 25, pp. 234–240 (1986)) to react in hexane at a temperature of from 60° to 90° C. for a period of from 1 to 20 hours, followed by cooling, filtering the reaction mixture through a glass filter, washing the filter cake with hexane, and then drying.

The thus obtained [RuCl(PPh$_3$)$_2$(dma)]$_2$($\mu$-Cl)$_2$ is then used as an intermediate for preparing the compound of formula (I) wherein R and R$^1$ both represent a phenyl group; R$^2$ represents a hydrogen atom; and X represents a chlorine atom. That is, [RuCl(PPh$_3$) (BINAP)]$_2$($\mu$-Cl)$_2$ can be obtained quantitatively by, for example, reacting the above-obtained intermediate complex and BINAP in a solvent, e.g., chlorobenzene, o-dichlorobenzene, methylene chloride, and 1,2-dichloroethane, at a temperature of from 50° to 100° C. for a period of from 5 to 20 hours and removing the solvent from the reaction mixture by distillation under reduced pressure.

Analyses such as elementary analysis proved that the thus obtained ruthenium-phosphine complex according to the present invention is a pure complex. This complex is so stable that the initial catalyst activity can be maintained even after 10 days' exposure in air. When applied to asymmetric hydrogenation, it shows high activity. In more detail, by using the complex catalyst of the present invention at a 1/100 to 1/1000 molar concentration based on a substrate, the reaction smoothly proceeds to give a hydrogenation product excellent in purity and optical purity.

Specific examples of the ruthenium-phosphine complexes of formula (I) according to the present invention other than the above-described one are shown below, which can be synthesized in the same manner as described above but starting with appropriately selected raw materials.

---

[RhCl(PPh$_3$)(p-Tol-BINAP)$_2$($\mu$-Cl)$_2$
[RhCl(PPh$_3$)(p-MeO-BINAP)]$_2$($\mu$-Cl)$_2$
[RuCl(PPh$_3$)(p-t-Bu-BINAP)]$_2$($\mu$-Cl)$_2$
[RuBr(PPh$_3$)(BINAP)]$_2$($\mu$-Br)$_2$
[RuBr(PPh$_3$)(p-Tol-BINAP)]$_2$($\mu$-Br)$_2$
[RuBr(PPh$_3$)(p-MeO-BINAP)]$_2$($\mu$-Br)$_2$
[RuBr(PPh$_3$)(p-t-Bu-BINAP)]$_2$($\mu$-Br)$_2$
[RuI(PPh$_3$)(BINAP)]$_2$($\mu$-I)$_2$
[RuI(PPh$_3$)(p-Tol-BINAP)]$_2$($\mu$-I)$_2$
[RuI(PPh$_3$)(p-MeO-BINAP)]$_2$($\mu$-I)$_2$
[RuI(PPh$_3$)(p-t-Bu-BINAP)]$_2$($\mu$-I)$_2$

---

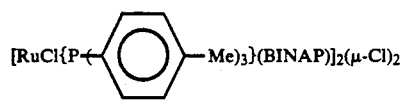

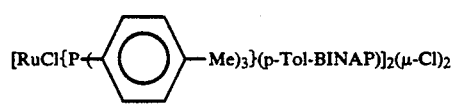

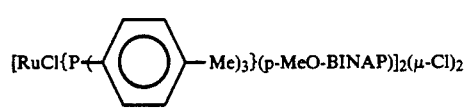

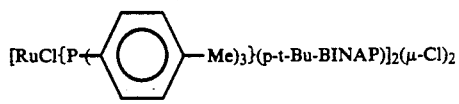

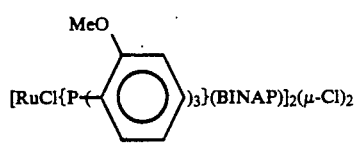

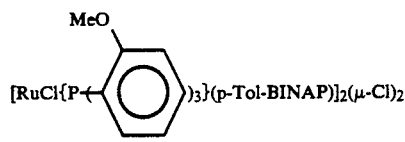

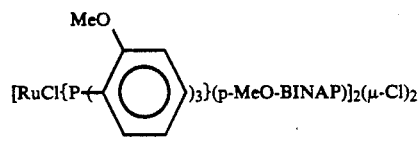

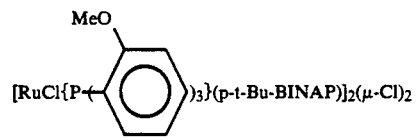

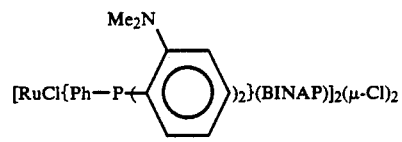

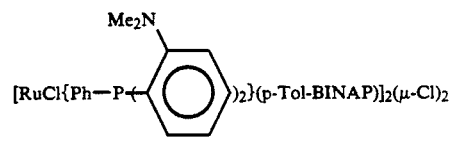

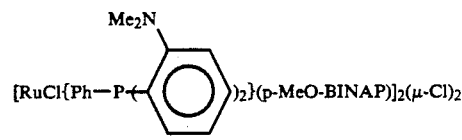

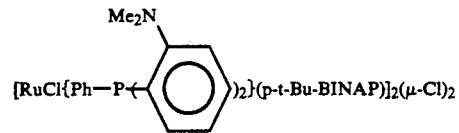

In the above formulae, abbreviations have the following meanings.

Ph: phenyl group
Me: methyl group
p-Tol-BINAP: 2,2'-bis(di-p-tolylphosphino)-1,1'-binaphthyl
p-MeO-BINAP: 2,2'-bis(di-p-methoxyphenylphosphino)-1,1'-binaphthyl
p-t-Bu-BINAP: 2,2'-bis(di-p-t-butylphenylphosphino)-1,1'-binaphthyl All the above illustrated ruthenium-phosphine complexes are also very stable complexes and, when used in asymmetric hydrogenation reactions, exhibit high activity and produce markedly excellent results as industrial catalysts.

The present invention is now illustrated in greater detail with reference to Examples and Application Examples, but it should be understood that the present invention is not construed as being limited thereto. All the percents are by weight unless otherwise indicated.

Measuring instruments used in Examples are as follows.

Gas chromatography:
Chromatograph: Shimadzu GC-9A (manufactured by Shimadzu Corporation)
Column: PEG-HT silica capillary (0.25 mm (d)×25 m (h)) (manufactured by Gasukuro Kogyo K.K.)
Measuring Temperature: from 100° to 200° C. at a rate of temperature rise of 3° C./min
High performance liquid chromatography (HPLC):
Pump: Waters Model 510 (manufactured by Waters Inc.)
UV Detector: Waters Model 484 (manufactured by Waters Inc.)
Column: YMC-Pack 002-3 SIL and YMC-Pack 003-3 SIL (both manufactured by Yamamura Kagaku Kenkyusho K.K.)
Developing solution: hexane:diethyl ether=9:1 (by volume); flow rate: 1 ml/min
Optical Rotation: DIP-181 (manufactured by Nippon Bunko Kogyo K.K.)
Elemental Analysis: PERKIN-ELMER 2400CHN (manufactured by Perkin-Elmer Co.)
$^{31}$P-NMR JNM-GX400 (manufactured by JEOL Ltd.)
External Standard: 85% $H_3PO_4$

EXAMPLE 1

Synthesis of [RuCl(PPh$_3$)$_2$(dma)]$_2$($\mu$-Cl)$_2$
(Chlorobis(tri-phenylphosphine)dimethylacetamido-ruthenium-$\mu$-chloro Dimer)

In 200 ml of N,N-dimethylacetamide were dissolved 10 g (45 mmole) of RuCl$_3$.3H$_2$O (ruthenium chloride trihydrate) and 24 g (91.5 mmole) of triphenylphosphine, followed by stirring at room temperature for 10 days. The precipitated green crystal was collected by filtration, washed with N,N-dimethylacetamide, and dried under reduced pressure to obtain 27.4 g (percent yield: 79%) of [RuCl$_3$(PPh$_3$)$_2$(dma)](dma) (trichloro-bis (triphenylphosphine)-dimethylacetamido-ruthenium-dimethylacetamide) as a green solid.

To 4.55 g of the resulting product was added 300 ml of hexane, and the mixture was heated in a closed tube on an oil bath at 90° C. for 16 hours. After cooling to room temperature, the supernatant liquor was removed, and the residual yellowish brown solid was washed twice with 50 ml portions of hexane, and dried under reduced pressure to obtain 4.5 g (percent yield: 99%) of the titled compound as a yellowish brown solid.

Elemental Analysis for C$_{40}$H$_{39}$Cl$_2$NOP$_2$Ru: Calcd. (%): C 61.31; H 5.02; N 1.79. Found (%): C 61.32; N 5.03; N 1.78.

EXAMPLE 2

Synthesis of [RuCl(PPh$_3$) ((+)-BINAP)]$_2$($\mu$-Cl)$_2$
(Chloro-triphenylphosphine-[(+)-2,2'-bis(diphenylphosphino)-1,1'-binaphthyl]ruthenium-$\mu$-chloro Dimer In 40 ml of dichloroethane were dissolved 0.52 g (0.5 mmole) of [RuCl(PPh$_3$)$_2$(dma]$_2$($\mu$-Cl)$_2$ obtained in Example 1 and 0.50 g (0.8 mmole) of (R)-BINAP, and the solution was heated in a closed tube at 90° C. for 16 hours and then freed of the solvent by distillation. To the residue was added 20 ml of hexane, and the mixture was placed in a ultrasonic cleaner for 2 to 3 minutes. The supernatant was removed, and the cleaning operation was repeated two more times to obtain 0.85 g (percent yield: 100%) of the titled compound as a brown solid.

Elemental Analysis for C$_{62}$H$_{47}$Cl$_2$P$_3$Ru: Calcd. (%): C 70.45; H 4.48; N 0. Found (%): C 69.70; H 4.56; N 0.

APPLICATION EXAMPLE 1

Synthesis of Methyl (3R)-(−)-3-Hydroxybutyrate

In a 200 ml stainless steel autoclave whose atmosphere had been displaced with nitrogen were charged 11.6 g (0.1 mole) of methyl acetoacetate and 50 ml of methanol, and 106 mg (0.05 mmole) of [RuCl(PPh$_3$) ((+)-BINAP)]$_2$($\mu$-Cl)$_2$ synthesized in Example 2 was added thereto to effect hydrogenation at a hydrogen pressure of 100 atm at 24° C. for 40 hours. After completion of the reaction, the solvent was removed by distillation, and the residue was distilled under reduced pressure to obtain 11.6 g (percent yield: 98%) of methyl (3R)-(−)-3-hydroxybutyrate. The product was found to have a purity of 99.0% by gas chromatography. The optical rotation $\alpha_D^{20}$ (neat) was −23.92°.

The resulting alcohol (30 mg) was esterified with (+)-$\alpha$-methoxy-$\alpha$-trifluoromethylphenylacetic acid chloride. As a result of HPLC, the resulting ester (designated MTPA ester) was found to be a mixture comprising 98.75% of methyl (3R)-(−)-hydroxybutyrate and 1.25% of methyl (3S)-(+)-3-hydroxybutyrate, revealing an optical purity 97.5% ee of methyl (3R)-(−)-3-hydroxybutyrate.

APPLICATION EXAMPLE 2

Synthesis of Methyl (3R)-(−)-Hydroxybutyrate

Asymmetric hydrogenation of methyl acetoacetate was carried out in the same manner as in Application Example 1, except that the ruthenium complex catalyst prepared in Example 2 had been allowed to stand in air for 10 days before use. The reaction results were as follows.

Yield: 11.6 g (percent yield: 98%)
Purity (gas chromatography): 98.8% $\alpha_D^{20}$ (neat): −23.94°
HPLC Analysis on MTPA ester:
Methyl (3R)-(−)-3-hydroxybutyrate=98.8%
Methyl (3S)-(+)-3-hydroxybutyrate=1.2%
Optical purity: 97.6% ee

REFERENCE EXAMPLE 1

Synthesis of Ru$_2$Cl$_4$[(+)-BINAP]$_2$(NEt$_3$)
(Di[2,2'-bis(diphenylphosphino)-1,1'-binaphthyl)tetrachloro-dirutheniumtriethylamine To 100 ml of toluene were added 1 g (3.56 mmole) of [RuCl$_2$(COD)]$_n$ (wherein COD represents cycloocta-1,5-diene), 2.66 g (4.27 mmole) of (+)-BINAP, and 1.5 g of triethylamine in a nitrogen atmosphere, and the mixture was heated at reflux for 10 hours. The solvent was removed by distillation under reduced pressure, and the residual crystal was dissolved in methylene chloride, filtered through Celite, and the filtrate was concentrated to dryness to obtain 3.7 g of the titled compound as a deep brown solid.

Elemental Analysis for $C_{94}H_{79}Cl_4NP_4Ru_2$: Calcd. (%): Ru 11.96; C 66.85; H 4.71; P 7.33. Found (%): Ru 11.68; C 67.62; H 4.97; P 6.94. $^{31}$P-NMR (CDCl$_3$) δppm: 51.06 (s), 51.98 (s), 53.87 (s), 54.83 (s)

COMPARATIVE EXAMPLE 1

Synthesis of Methyl (3R)-(−)-3-Hydroxybutyrate

The same procedures as in Application Example 1 were repeated, except for using 84.5 mg of Ru$_2$Cl$_4$((+)-BINAP)$_2$(NEt$_3$) synthesized in Reference Example 1. The reaction results were as follows.

Yield: 11.6 g (percent yield: 98%)
Purity (gas chromatography): 99.0%
$\alpha_D^{20}$ (neat): −24.17°
HPLC Analysis on MTPA ester:
Methyl (3R)-(−)-3-hydroxybutyrate=99.55%
Methyl (3S)-(+)-3-hydroxybutyrate=0.45%
Optical purity: 99.1% ee

COMPARATIVE EXAMPLE 2

Synthesis of Methyl (3R)-(−)-3-Hydroxybutyrate

The same procedures as in Comparative Example 1 were repeated, except for allowing Ru$_2$Cl$_4$((+)-BINAP)$_2$(NEt$_3$) to stand in air for 10 days before use. The reaction results were as follows.

Yield: 10.4 g (percent yield: 89%)
Purity (gas chromatography): 99%
$\alpha_D^{20}$ (neat): −23.63°
HPLC Analysis on MTPA ester:
Methyl (3R)-(−)-3-hydroxybutyrate=98.4%
Methyl (3S)-(+)-3-hydroxybutyrate=1.6%
Optical purity: 96.8% ee As is apparent from the results of the foregoing Application Examples and Comparative Examples, the rutheniumphosphine complex according to the present invention undergoes no reduction in either catalytic activity or optical purity of the product even when exposed in air as compared with the conventional complex catalyst.

The present invention provides a novel ruthenium-phosphine complex which exhibits excellent performance properties as a catalyst for various organic synthesis reactions and asymmetric hydrogenation reaction. For example, it attains industrially superior results in selective hydrogenation of olefins while showing excellent catalytic activity. In addition, the ruthenium complex of the present invention can be prepared at lower cost than conventional rhodium complex catalysts, thus contributing to a reduction of price of the final products. The complex of the present invention is therefore of high industrial value.

While the invention has been described in detail and with reference to specific examples thereof, it will be apparent to one skilled in the art that various changes and modifications can be made therein without departing from the spirit and scope thereof.

What is claimed is:

1. A ruthenium-phosphine complex represented by formula (I):

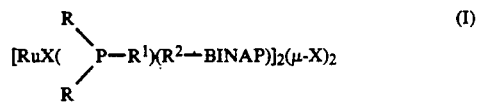

wherein R$^2$-BINAP represents a tertiary phosphine compound represented by formula (II):

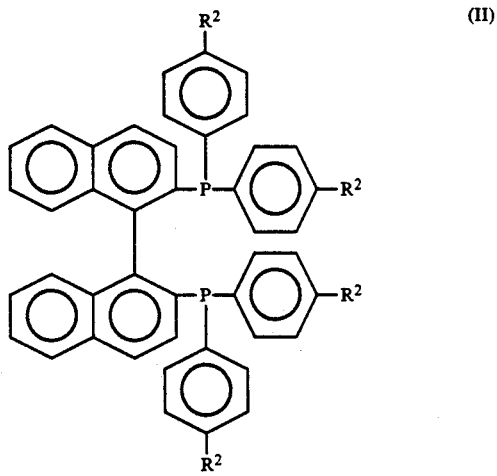

wherein R$^2$ represents a hydrogen atom, a methyl group, a methoxy group, or a t-butyl group; X represents a halogen atom; and R and R$^1$, which may be the same or different, each represent a phenyl group or a substituted phenyl group.

2. A ruthenium-phosphine complex represented by formula (III):

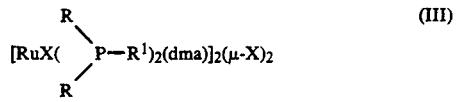

wherein R and R$^1$, which may be the same or different, each represent a phenyl group or a substituted phenyl group; and dma represents N,N-dimethylacetamide.

* * * * *